United States Patent [19]

George et al.

[11] 4,122,118
[45] Oct. 24, 1978

[54] COPPER-N-METHYLPYRROLIDONE CATALYST USEFUL IN THE PRODUCTION OF NITRODIPHENYL AMINES

[75] Inventors: Joachim George, Leverkusen; Joachim Repplinger, Koenigsdorf, both of Germany

[73] Assignee: Bayer Aktiengesellschaft, Germany

[21] Appl. No.: 818,205

[22] Filed: Jul. 22, 1977

[30] Foreign Application Priority Data

Jul. 28, 1976 [DE] Fed. Rep. of Germany ....... 2633811

[51] Int. Cl.$^2$ .................... C07C 85/04; C07D 207/26; B01J 31/02
[52] U.S. Cl. .................................. 260/576; 252/430; 260/326.22
[58] Field of Search ...................... 260/326.45, 326.22, 260/576; 252/428, 430

[56] References Cited

U.S. PATENT DOCUMENTS

| 2,700,060 | 1/1955 | Cherlow et al. ............... 260/576 X |
| 3,313,854 | 4/1967 | Levy .................................. 260/576 |
| 3,393,241 | 7/1968 | Nielsen ............................... 260/576 |
| 3,699,085 | 10/1972 | Johnson ............................ 260/78 A |

OTHER PUBLICATIONS

Newman et al., "J. Org. Chem.", vol. 26, p. 2525, (1961).
Fine Chemicals Patents Journal, vol. 8, No. 10, British 5:4–5:5, (3-13-68).

Primary Examiner—Winston A. Douglas
Assistant Examiner—John J. Doll
Attorney, Agent, or Firm—Connolly and Hutz

[57] ABSTRACT

Catalyst consisting of a reaction product of a copper compound with N-methyl-pyrrolidone which accelerates the reaction of nitrochlorobenzenes with aromatic amines.

3 Claims, No Drawings

COPPER-N-METHYLPYRROLIDONE CATALYST USEFUL IN THE PRODUCTION OF NITRODIPHENYL AMINES

This invention relates to a catalyst and to a process for the production of nitrodiphenyl amines by reacting nitrochlorobenzenes with aromatic amines in the presence of potassium carbonate.

The reaction of nitrochlorobenzenes with aromatic amines is described in numerous literature references. Patent Specifications as old as U.K. patent specification No. 24,091, German Patent Specification No. 185,663 and French Patent Specification No. 381,230 mention the use of alkali carbonates and copper compounds as catalysts. The extraordinarily slow reaction can be further accelerated by using special amides or amines with the copper salt. Unfortunately, the compounds used are all attended by disadvantages. Thus, dimethylformamide according to U.K. patent specification No. 839,420 is volatile under the reaction conditions and forms secondary products which are difficult to remove.

Hexamethyl phosphoric acid triamide according to U.K. patent specification No. 839,420 and formanilide according to U.S. Pat. No. 3,313,854, when used in catalytic quantities, show inadequate accelerating properties in the presence of copper compounds. Dimethyl sulphoxide according to U.S. Pat. No. 3,277,175, acetanilide according to NL-OS No. 6,506,527 and salicylanilide according to FR-PS No. 1,203,810 also all produce only weak effects. The secondary products which are formed to a certain extent and which are difficult to remove detract from the quality of the nitrodiphenyl amine obtained.

Accordingly, the object of the present invention is to provide a catalyst which does not have any of the disadvantages referred to above. It has now been found that a catalyst consisting of a reaction product of copper compounds with N-methylpyrrolidone has an excellent accelerating effect and can be used with advantage in the reaction of nitrochlorobenzenes with aromatic amines.

Accordingly, the present invention provides a catalyst consisting of the reaction product of a copper compound with N-methylpyrrolidone. The invention also provides a process for the production of nitrodiphenyl amines which can be obtained by reacting nitrochlorobenzenes with aromatic amines in the presence of potassium carbonate which is characterised by the fact that the reaction is accelerated by the described catalyst.

The copper compounds used for producing the catalysts are copper salts of weak, medium-strength or strong acids. The following salts are mentioned by way of example: CuO, $CuCO_3$, basic $CuCO_3$, $CuSO_4$, $CuCl_2$, $Cu(NO_3)_2$, $Cu(CH_3COO)_2$, $Cu(HCOO)_2$; CuCN.

It is preferred to use copper salts of weak or medium-strength acids and particularly preferred to use copper salts of weak acids, especially CuO, $CuCO_3$, basic $CuCO_3$ and CuCN.

The molar ratio of copper compound (A) to N-methylpyrrolidone (B) in the reaction product amounts to between 2 : 1 and 1 : 10 and preferably to between 1 : 3 and 1 : 5.

The catalyst can be produced by reacting the components in the milar ratios indicated at temperatures of from 100° C. to 200° C. and preferably at temperatures of from 150° C. to 180° C.

The copper compound is heated with N-methylpyrrolidone until it has passed into solution. By adding an aromatic solvent, such as xylene for example, the catalyst is precipitated in the form of a light brown powder and can be filtered off and dried. The complex can also be produced in the presence of solvents, preferably aromatic amines, such as aniline, toluidine, etc.

The catalyst according to the invention can be used for example for accelerating the reaction of nitrochlorobenzenes with aromatic amines to form nitrodiphenyl amines.

The nitrochlorobenzenes used for this reaction may be compounds corresponding to the formula (I)

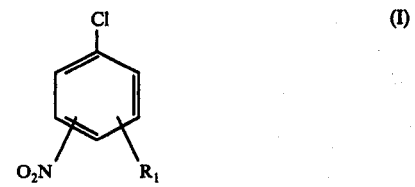

in which $R_1$ represents hydrogen or an alkyl group and the nitro group is in the o-, m- or p- position to the chlorine group. It is preferred to use compounds (I) in which the nitro group is in the p- position. The substituent $R_1$ preferably represents hydrogen or $C_1$ - $C_3$ alkyl, more especially hydrogen or methyl.

The following compounds are specifically mentioned as compound corresponding to formula (I) above: p-nitrochlorobenzene, o-nitrochlorobenzene, 4-nitro-3-methyl chlorobenzene and 4-nitro-2-methyl chlorobenzene.

The aromatic amines used are compounds corresponding to formula (II)

in which $R_2$ represents hydrogen or an alkyl group and is in the o-, m- or p-position to the amino group. Preferred compounds are those in which $R_2$ is in the m- or p position, more especially in the p- position. The substituent $R_2$ is, with particular preference, hydrogen or $C_1$ - $C_3$ alkyl, more especially hydrogen or methyl.

For the purposes of illustration, the following compounds are mentioned by name: aniline, ortho-, meta -, para-toluidine, 4-ethylaniline and 4-isopropylaniline.

The reactants are reacted in the presence of potassium carbonate, as far as possible under anhydrous conditions. To this end, the water of reaction is formed is continuously distilled off azeotropically with an entraining agent. The following compounds, for example, represent suitable entraining agents: benzene, toluene, xylene, chlorobenzene, chlorotoluenes, aniline and toluidines.

Xylene, aniline, o-, m- and p- toluidine are mentioned as examples of the solvents in which the compounds of formula (I) and (II) are reacted.

From 1 to 4 moles, preferably from 2 to 3 moles and, with particular preference, from 1.8 to 2.5 moles of the aromatic amine are used per mole of nitrochlorobenzene. Potassium carbonate is added in a quantity of from 50 to 80% by weight and preferably in a quantity of 66% by weight, based on p-nitrochlorobenzene. The catalyst according to the invention is used in a quantity sufficient to produce a catalytic effect. For example, these quantities amount to between 0.5 and 10% by weight and preferably to between 5 and 7% by weight, based on nitrochlorobenzene.

There is no need to add the catalyst pre-formed to the reaction solution. It can also be formed in a preliminary reaction, preceding the nitrodiphenyl amine reaction, of copper salts with N-methyl-pyrrolidone in the presence of the compounds of formula (I) and/or (II) in the reaction solution. However, it is important to ensure that the reaction of the compounds of formulae (I) and (II) does not begin until the catalyst has been formed.

The reaction temperatures required for the formation of nitrodiphenyl amines are known to the average expert and are generally in the range from 150° C. to 220° C. and preferably in the range from 170° C. to 205° C.

The nitrodiphenyl amines produced by the process according to the invention correspond to the formula (III)

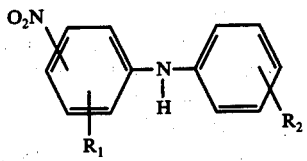

in which $R_1$ and $R_2$ are as previously defined.

The following compounds are mentioned by way of example: p-nitrodiphenyl amine, 4'-methyl-p-nitrodiphenyl amine and 3'-methyl-p-nitrodiphenyl amine.

The nitrodiphenyl amines produced by the process according to the invention are valuable intermediate products for the production of, for example, dyes or stablisers for rubbers. They can readily be reduced by known methods to form amino diphenyl amines.

The invention is illustrated by the following Examples.

EXAMPLE 1

93 g of aniline, 157 g of p-nitrochlorobenzene, 2 g of CuO, 150 g of xylene and 12 g of N-methylpyrrolidone were heated under reflux for 20 minutes to 160° C. on a water separator. 100 g of dry potash and 93 g of aniline were then added and the condensation reaction was started by increasing the temperature to 185° C. After 10 hours, 9 g of water had formed and the reaction had ceased. The mixture was suspended in water, sodium hydroxide (5 g) was added and all the volatile constituents were then distilled off with steam. At the same time, the crude nitrodiphenyl amine formed into granules and was isolated and dried. Yield of 4-nitrodiphenyl amine: 209 g, mp.118° C. 106.8 g of aniline and 6.1 g of p-nitrochlorobenzene were recovered from the steam distillation condensate.

EXAMPLE 2

The reaction mixture and procedure were the same as described in Example 1, except that CuCN was used. Yield of 4-nitrodiphenyl amine: 208.5 g, mp. 123° C. 105.4 g of aniline and 6.2 g of p-nitrochlorobenzene were recovered in the same way as in Example 1.

EXAMPLE 3

The reaction mixture and procedure were as in Example 1 except that 6 g of $2CuCO_3 \cdot Cu(OH)_2$ were used. Yield of 4-nitrodiphenyl amine: 208.0 g, mp. 119° C. 106.1 g of aniline and 6.1 g of p-nitrochlorobenzene were recovered in the same way as in Example 1.

EXAMPLE 4

2 g of CuO, 12 g of N-methylpyrrolidone and 93 g of aniline were heated to 160° C. The copper oxide dissolved over a period of 20 minutes. This solution was added dropwise over a period of 30 minutes to a mixture, boiling at 180° C., of 157 g of p-nitrochlorobenzene, 93 g of aniline, 10 g of xylene and 100 g of potash. The temperature was then increased to 188° C. and the further reaction carried out in the same way as described in Example 1. Yield of 4-nitrodiphenyl amine 209 g, mp. 117.5° C. 107.2 g of aniline and 6.7 g of p-nitrochlorobenzene were recovered in the same way as in Example 1.

EXAMPLE 5

107 g of p-toluidine, 157 g of p-nitrochlorobenzene 3 g of CuO, 150 g of xylene and 14 g of N-methylpyrrolidone were heated under reflux for 20 minutes to 160° C. on a water separator. 105 g of dry potash and 107 g of p-toluidine were then added and the condensation reaction was initiated by increasing the temperature to 185° C. After 12 hours, 9 g of water collected in the water separator and the reaction had ceased. The mixture was suspended in the same batch of water. 6 g of sodium hydroxide (45%) were added and all the volatile constituents were then distilled off with steam. At the same time, the crude 4-methyl-4'-nitrodiphenyl amine was granulated. Yield of 4-methyl-4'-nitrodiphenyl amine: 219 g, mp: 122° C. 122.0 g of p-toluidine and 7.2 g of p-nitrochlorobenzene were recovered from the steam distillation condensate.

EXAMPLE 6

93 g of aniline, 157 g of o-nitrochlorobenzene, 2 g of CuO, 150 g of xylene, 12 g of N-methylpyrrolidone, 93 g of aniline and 100 g of potash were reacted in the same way as described in Example 1. Yield of 2-nitrodiphenyl amine: 201 g, mp: b 110° C. 109 g of aniline and 8 g of o-nitrochlorobenzene were recovered from the steam distillation condensate

We claim:
1. In the process of producing a nitrodiphenyl amine by reacting a nitrochlorobenzene with an aromatic amine in the presence of a copper containing catalyst and, as halogen acceptor, potassium carbonate, the improvement which comprises utilizing, as the copper containing catalyst, the reaction product of a copper compound with N-methylpyrrolidone.
2. The process of claim 1 wherein the molar ratio of said copper compound to N-methylpyrrolidone in said reaction product is from 2:1 to 1:10.
3. The process of claim 1 wherein said copper compound and N-methylpyrrolidone are reacted at a temperature of from 120° to 200° C. to form said reaction product.

* * * * *